ROSE PLANT "PINK SACHET"
Filed Oct. 17, 1975
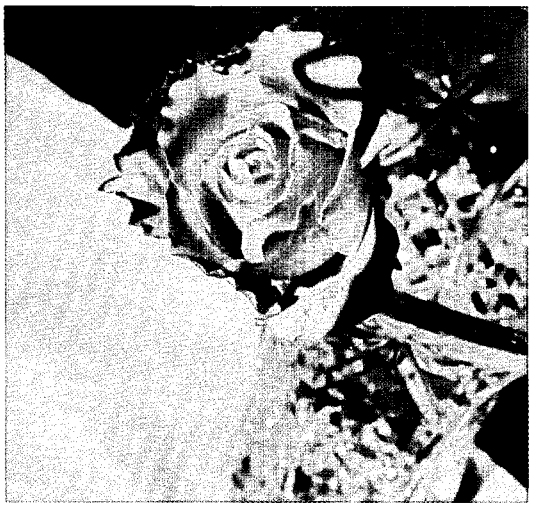
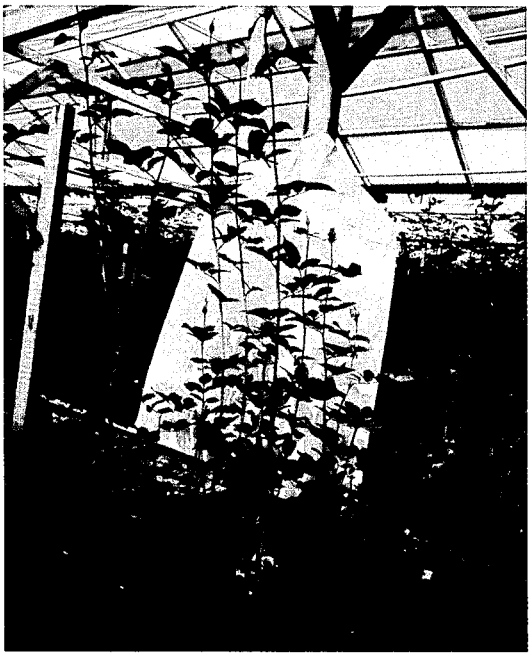

United States Patent

Plant Pat. 3,959
Patented Oct. 19, 1976

3,959

ROSE PLANT "PINK SACHET"

George Y. Umeda and Daniel S. Shinoda, San Leandro, Calif., assignors to San Lorenzo Nursery Company, San Leandro, Calif.

Filed Oct. 17, 1975, Ser. No. 623,459
**Int. Cl.[2] A01H *5/00***
U.S. Cl. Plt.—18 1 Claim

ABSTRACT OF THE DISCLOSURE

A new variety of rose plant distinguished by its continuous production of roseine purple blooms and an exceptionally long lasting quality as cut flowers with a very heavy fragrance, the plant having a vigorous growth habit with the flowers being of medium size and with long stems of good strength.

BACKGROUND OF THE NEW PLANT

This new variety of rose plant originated as a seedling from a cross of "Yuletide" (P.P. 1,391) and "Snowsong Supreme" (P.P. 2,624) made by us during breeding efforts carried on by us at San Lorenzo Nursery, at San Leandro, Calif., since June 19, 1972, in its greenhouses with the object of producing commercial cut flowers for the market with blended color while retaining the fragrance of "Snowsong Supreme." Asexual reproduction of this plant by buddings and potting in a propagating house in greenhouse bed, carried on by us at San Leandro, Calif., since 1972, demonstrated that the desirable characteristics were well fixed, and propagation through successive generations by budding has shown the novel features to hold true from generation to generation.

DESCRIPTION OF THE DRAWING

Our new variety of rose plant is illustrated by the accompanying full color photographic drawing, in which:

FIG. 1 is a full face view of one of the blossoms on a stem, and

FIG. 2 is a full view of several plants in a bed in a greenhouse.

The colors shown being as nearly true as is possible to obtain by conventional photographic procedures, the true color of roseine purple being shown in the color swatch appearing below the photographs.

DESCRIPTION OF THE NEW PLANT

The following is a detailed description of the rose plant with specifications of color according to Robert S. Wilson's Horticultural Colour Chart as issued by The British Colour Council and The Royal Horticultural Society.

The plant

Origin: Seedling.
Parentage:
*Seed parent.*—"Yuletide," P.P. 1,391.
*Pollen parent.*—"Snowsong Supreme," P.P. 2,624.
Classification:
*Botanic.*—Rosa hybrid.
*Commercial.*—Hybrid tea.
Form: Not bushy. Grows straight upward.
Height: To 60 to 65 inches.
Growth: Average rate.
Habit: Tall, upright and branched.
Strength: Very good.
*Stem length.*—About 22 to 30 inches. Upper stem diameter—about ¼ inch. Lower stem diameter—about ½ inch.

Foliage: Quantity—abundant. About 8 leaves.
*Leaves.*—Shape—ovate with margin serrated. Size: 6 x 5 inches. Texture: Smooth and glossy. Color: Upper side—Green, 139A. Lower side—Green, 137C.
*Leaflets.*—5 in number. Size: About 3 x 2 inches. Petioles: Length—¾ inch. Ribs and veins: Yes. Rachis: No. Color: Substantially the same as full grown leaf. Thorns: Yes, very few, located on lower stem, the upper stem being substantially free of thorns. Color—Grey-Brown, 195A.

The bud

Size: Medium, about ¾ inch in diameter with a depth of 1¼ inches.
Form: Long, pointed and ovoid.
Opening rate: Slow.
Sepals: Stand up and pointed.
*Colors.*—Inside—Greyed-Green, 195A. Outside—Lettuce Green, 144A. When sepals first divide, the color is Red-Purple, 66C, and when petals begin to unfurl, the color is Red-Purple, 67C.
Calyx: Funnel shaped and broad. Does not split.
*Aspect.*—Smooth.
Peduncle: Length—3 inches. Slender and not hairy.
*Color.*—Scheeles Green, 144B.

The flower

Blooming habit: Spring, midseason and fall. Profusely and continuously.
Size: Medium. 5 inches in diameter and 2 inches in depth.
Borne: Singly.
Shape: When bloom first opens it is cup shaped, with high center, and does not change form later.
Petalage: 33 petals in loose arrangement, and in cupped form, with margins ruffled.
*Color.*—Outer petals—Roseine-Purple, 68A. Base, Orange-Buff, 20C. Inside petals—Roseine-Purple, 68C. Base, Orange-Buff, 20C. Reverse side—Red-Purple, 73B. Petals stay on stem approximately 12 days.
*Texture.*—Leathery.
*Appearance.*—Satiny.
Petaloids: 4 in number.
*Size.*—¾ inch.
*Color.*—Rhodamine-Purple, 68D.
Peduncle: Length—about 3 inches. Sturdy and upright.
*Color.*—Scheeles Green, 144B.
Discoloration: No, after full bloom.
Effect of weather: Not affected by wet or hot weather.
Persistence: Petals do not hang on and dry.
Disease resistance: Not known.
Fragrance: Very heavy.
Lasting quality:
*On plant.*—10 days.
*As cut flower.*—7 to 10 days.

Reproductive organs

Stamens:
*Anthers.*—About 70, curved arrangement and about ⅛ inch long.
*Filaments.*—About ¾ inch long. Color: Indian Lake, 58A.
*Pollen.*—Color—Yellow-Green, 154C.
Pistils: About 50 in number.
*Length.*—¼ inch.
*Stigmas.*—Color—Red-Purple, 60B.
Characteristics of ovaries: Color—Greyed-Green, 193C.

Fruit

Fertile: Yes.
Shape: Ovoid.
Color at maturity: Yellow-Green, 152B.

This variety of rose plant is a continuous grower. Its blossom color is outstanding and distinctly different than either of its parent varieties, has a heavy fragrance and, with the advantageous plant habit, this new plant is outstanding as a cut commercial rose with very long, strong stems.

We claim:

1. A new and distinct variety of rose plant, substantially as herein shown and described, characterized by the roseine-purple coloring of its medium-sized, high centered blossoms which are produced continuously from the spring to the fall and profusely on vigorous, upright, much branched plants which reach a height of 60 to 65 inches, the cut flowers having long lasting quality with a heavy fragrance and with stems of an average length of 22 to 30 inches of excellent strength, with substantially no thorns on the upper stem and very few on the lower stem.

No references cited.

ROBERT E. BAGWILL, Primary Examiner